United States Patent [19]

Moore

[11] Patent Number: 5,063,920
[45] Date of Patent: Nov. 12, 1991

[54] HALO FIXATION DEVICE AND METHOD OF USE

[76] Inventor: W. Philip Moore, 1250 Willow Branch Ave., Jacksonville, Fla. 32205

[21] Appl. No.: 580,603

[22] Filed: Sep. 11, 1990

[51] Int. Cl.[5] .............................................. A61F 5/01
[52] U.S. Cl. ................. 128/87 B; 128/84 C; 128/76 R; 128/DIG. 19
[58] Field of Search ............. 128/845, 846, 869, 870, 128/874, 84 C, 87 R, 87 B, 89 A, 76 R, DIG. 19

[56] References Cited

U.S. PATENT DOCUMENTS

| 4,010,881 | 4/1991 | Boudreau et al. | 128/87 B X |
| 4,407,274 | 10/1983 | Goodley | 128/87 B X |
| 4,538,598 | 9/1985 | Gill et al. | 128/84 C |
| 4,541,421 | 9/1985 | Iversen et al. | 128/87 B |
| 4,620,530 | 11/1986 | Lanier et al. | 128/87 B X |
| 4,730,606 | 3/1988 | Leninger | 128/84 C X |
| 4,890,605 | 1/1990 | Rosendale | 128/84 C X |
| 4,987,886 | 1/1991 | McDonald et al. | 128/84 C X |

FOREIGN PATENT DOCUMENTS 2403790  5/1979  France ................ 128/84 C

Primary Examiner—Robert A. Hafer
Assistant Examiner—Kevin G. Rooney
Attorney, Agent, or Firm—Thomas C. Saitta

[57] ABSTRACT

A device and method for immobilizing a person having cervical injuries in a bed having a rigid, horizontal frame member, the device comprising a halo for attachment to the person's head, anterior and posterior support rods, cross mmembers connecting the halo to the anterior and posterior support rods, and a vest having an anterior section only. The anterior support rods are attached to the vest, while the posterior support rods are attached to the horizontal frame member of the bed.

6 Claims, 1 Drawing Sheet

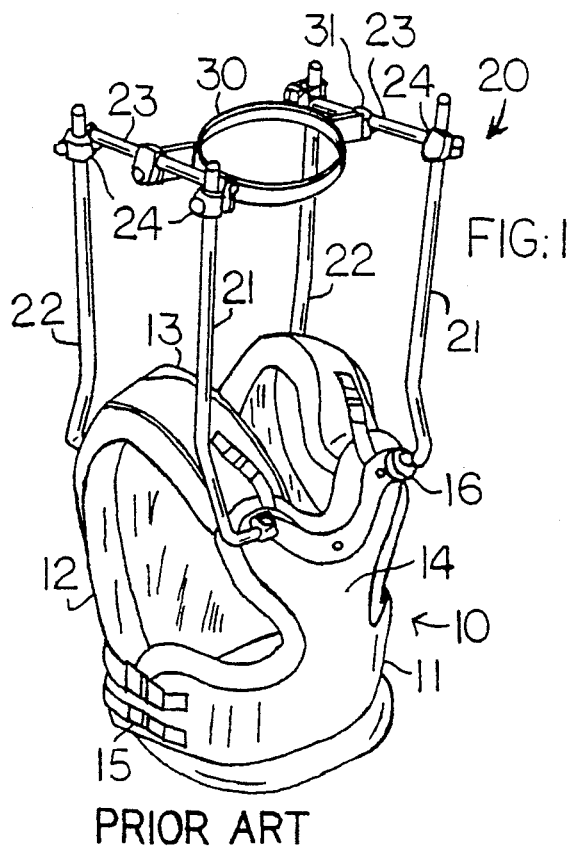
FIG. 1
PRIOR ART
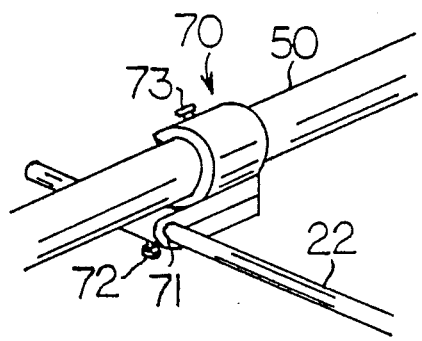
FIG. 3
FIG. 2
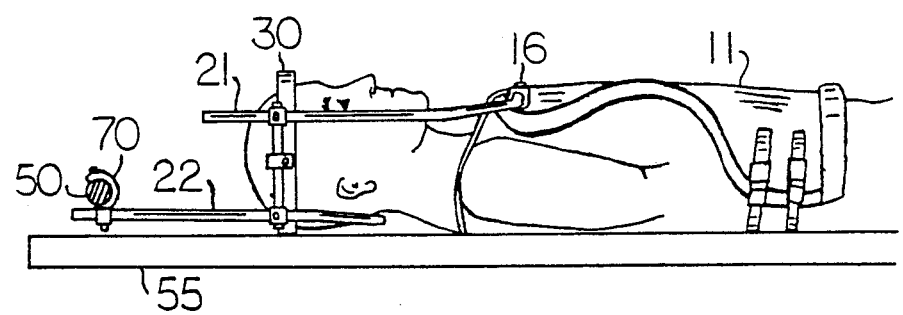

5,063,920

HALO FIXATION DEVICE AND METHOD OF USE

BACKGROUND OF THE INVENTION

The invention relates generally to the field of devices used for cervical immobilization in patients having cervical spine injuries, and to methods of immobilizing using such devices. More specifically, the invention relates to the field of such devices having structural support means attached to the patient's torso which immobilize a halo ring directly affixed to the skull of the patient, such that the patient's head is immobile relative to the torso. Even more specifically, the invention relates to a particular structure and method of use whereby such immobilization is accomplished by attachment of the structural support means to the bed itself as well as to the patient's torso.

For many years physicians have utilized halo fixator devices to treat cervical spine injuries. In general, the device consists of an annular metal halo which surrounds the patient's head and is attached by a number of pins directly to the skull. This halo is then fixedly attached to support means consisting of a number of cross members, anterior and posterior uprights or rod members. These support means are then attached to the torso of the patient, by a body cast or by a lightweight, adjustable vest of plastic or similar material. With the device in place and all components rigidly attached, the patient's head is immobilized relative to the patient's torso so that no cervical spine movement is possible. The vest is usually constructed to have an anterior and a posterior section which encase the patient and are joined by straps or other fastening means. The support means are usually two anterior and two posterior rods which are secured to the vest by fastening brackets, plus two cross member rods running laterally between each set of posterior and anterior rods. The halo is connected to the cross members.

In many instances the patient is required to remain in bed for long periods of time. Because of this period of forced immobility, and also because the patient frequently has loss of sensation due to the injuries sustained, the patient cannot shift or adjust body position and it is very common for the patient to develop pressure sores on the posterior side of the body. To minimize the development of pressure sores the patient should have cushioned posterior support with few areas of relatively hard surface or increased pressure points. The shift from body casts to lightweight vests has helped in this regard, but the posterior section of the vest is still a major source of pressure points causing the development of sores on the patient, since the vest is positioned between the bed itself and the patient, with the patient's body weight pushing continually down onto the vest.

The invention alleviates this problem by providing a device and method for immobilizing the patient's head relative to the torso which does not incorporate the posterior section of the vest. The patient therefore rests directly on the bed surface and any pressure points which would be caused by the use of a vest are removed. The anterior portion of the vest and the standard support means are still utilized to rigidly fix the halo in place, so that once the patient is no longer required to remain horizontal, the posterior section of the vest can be attached to the support means already in place. This is accomplished by providing means to attach the posterior support rods directly to the frame of the bed, while the anterior support rods are attached to the anterior section of the vest in the usual manner.

It is an object of this invention to provide a halo fixation device and method of use utilizing a two part vest, where the support means for immobilizing the patient's head relative to the patient's torso are attached directly to the frame of the bed such that the posterior portion of the vest is not required, while further allowing the support means to be detached from the bed frame and attached to the posterior portion of the vest if needed.

BRIEF SUMMARY OF THE INVENTION

The invention comprises a halo fixation device and its method of use, the devise comprising an annular halo for attachment directly to the skull of a patient, support means for connecting said halo to a vest secured to the patient's torso and to the frame of a bed, attachment means for affixing said support means to the vest and bed frame attachment means for affixing said support means to said bed frame. The vest comprises an anterior and a posterior section which are joined together by straps or other similar means. The support means comprise two posterior support rods, two anterior support rods, and two cross members. Said halo is attached to said cross members which run laterally between an anterior and a posterior support member. The anterior support rods are affixed to the anterior portion of the vest. When the patient is confined in the horizontal position, the posterior support rods are attached directly to the frame of the bed and only the anterior portion of the vest is secured to the patient's torso. Since the halo is anteriorly fixated by the anterior support rods attached to the vest and posteriorly fixated by the posterior support rods attached to the bed frame, the patient's head is immobilized relative to the torso and no independent movement is possible. When the patient improves to the point that confinement to the horizontal position is no longer required, the posterior support rods are detached from the bed frame, the posterior section of the vest is secured to the patient and attached to the anterior portion, and the posterior rods are then attached to the posterior section of the vest in the standard configuration.

DESCRIPTION OF THE DRAWINGS

FIG. 1 is a perspective view of prior art, showing a standard two part halo vest and support means.

FIG. 2 is a side view of the invention showing the device as attached directly to the bed frame.

FIG. 3 is a detail showing a posterior rod, bed attachment means and a portion of the bed frame.

DETAILED DESCRIPTION OF THE INVENTION

With reference to FIG. 1, a prior art device referred to as an halo vest is illustrated. The vest 10 comprises an anterior section 11 and a posterior section 12 and is made of a lightweight, relatively rigid plastic material. The vest 10 is shaped to enclose the torso of a patient by attaching the shoulder restraint members 13 of the posterior section 12 to the breast plate 14 of the anterior section 11 such that the patient's head extends between the shoulder restraints 13 and the patient's arms extend to each side. The lower portion of the posterior section 12 is attached to the lower portion of the anterior section 11 on each side of the patient's torso below the arms. The posterior section 12 and the anterior section 11 are usually connected to each other by adjustable strap and buckle means 15.

Halo support means 20 consist of a pair of anterior support rods 21, a pair of posterior support rods 22, and a pair of cross members 23. The anterior support rods 21 are attached to the anterior section 11 of the vest 10 and the posterior rods are attached to the posterior section 12 of vest 10 by vest bracket means 16. The anterior support rods 21 and the posterior support rods 22 are attached to the vest 10 so that they extend superiorly from the vest 20, relatively parallel to the longitudinal axis of the patient. In this manner the anterior support rods 21 and posterior support rods 22 provide a framework defining the corners of a rectangular cross-section. Cross members 23 are attached between an anterior support rod 21 and its corresponding posterior support rod 22 by support bracket means 24 such that one cross member 23 extends laterally on either side of the patient's head. The annular member or halo 30 is then attached to each cross member 23 by halo brackets 31.

To immobilize the cervical spine in cases of injury, the surgeon first attaches the annular member 30 directly to the skull of the patient. The posterior section 12 and the anterior section 11 of the vest 10 are then strapped to each other around the patient's torso. The anterior support rods 21 and the posterior support rods 22 are aligned and the cross members 23 are positioned at the proper location to receive the halo 30. Vest bracket means 16, support bracket means 24 and halo bracket means 31 allow movement of the various components during this adjustment phase. Upon proper positioning of all components, the brackets are tightened such that no movement of the halo 30, the cross members 23, the anterior support rods 21 and the posterior support rods 22 is possible. In this manner, the patient's head is fixed in position relative to the torso and the cervical spine is immobilized until the support means 20 are adjusted or removed. For a patient confined to a horizontal position, use of this device contributes to the creation of pressure sores due to the fact that the posterior section 12 of the vest 10 is beneath the patient.

With reference now to FIG. 2, the invention and its method of use are illustrated. The invention comprises the addition of removable bed frame attachment means 70 to the posterior support rods 22 of the support means 20. The device is now adapted to attach directly to a horizontal frame member 50 at the head of the patient's bed. The standard beds for containing patients having cervical injuries are constructed with a rigid and strong fixed horizontal frame member 50 for use in traction situations. The beds also have lateral bracing means or contoured indentions to further confine the patient's body. Utilization of the frame attachment means 70 allows for cervical immobilization without need for the posterior section 12 of the halo vest 10 while the patient is confined to the horizontal position. The posterior support members 22 are positioned relative to the cross members 23 such that their major portion extends superiorly above the cross members 23. Posterior support rods 22 are structured to be unobstructed over the major portion of their length so that they have free movement through the support member brackets 24 joining them to the cross members 23, when the support member brackets 24 are in the loosened condition. By this construction the posterior support rods 22 can be adjusted to remain in either the extreme superior position of FIG. 2 or in the standard position illustrated in FIG. 1.

Frame attachment means 70 are affixed to the superior portions of the posterior support rods 22, as shown in FIG. 3. The frame attachment means 70 comprise any suitable bracket means of known construction which provide for adjustable fixation on the posterior support rods 22 as well as adjustable placement on the frame member 50. The embodiment illustrated in FIG. 3 shows a frame attachment means 70 having a circular opening 74 to receive the frame member 50. The frame attachment means 70 can be positioned laterally on the frame member 50 and then fixed in position by tightening frame screw 73. A rod gripping aperture 71 receives the posterior support rod 22. The posterior support rod 22 is positioned superiorly within the frame attachment means 70 and fixed by tightening rod screw 72. It should be apparent that equivalent embodiments are within the realm of one skilled in the art, these equivalents requiring a structure allowing for both adjustment and fixation of the posterior support rods 22 laterally and superiorly.

To utilize the method of the invention, a patient with cervical injuries requiring immobilization has the annular member 30 attached to the skull in the usual manner. The anterior section 11 of a vest 10 is strapped onto the patient's torso and the anterior support rods 21 are attached in the usual manner. The annular halo member 30 is attached to the cross members 23. The posterior support rods 22 are extended superiorly above the cross members 23 and attached by the frame attachment means 50 to the horizontal frame member 50 of the bed. Upon proper positioning of all components, the various bracket means are tightened. The patient's cervical spine is now immobilized by the rigid framework now including the frame member 50 as a component. Additionally, the patient may be further immobilized by use of a thoracic strap attached to the bed itself, the strap extending across the vest 10. In situations where the bed has sufficient lateral bracing means and contoured confining portions to preclude movement, the anterior section 11 of the vest 10 need not be strapped directly to the patient's torso, the thoracic straps being sufficient to insure immobilization. Immobilization of the head relative to the torso is accomplished without need for the posterior section 12 of the vest 10. This reduces the pressure points present during the immobilization period and contributes to the lesser likelihood of development of pressure sores.

When the time comes that the patient need no longer be confined to the horizontal position, the rod screws 72 and support bracket means 23 are loosened and posterior support rods 22 are positioned to extend below the cross members 23. The posterior section 12 of vest 10 is placed on the patient and connected to the anterior section 11. The posterior support rods 22 are inserted into the vest bracket means 16 of the posterior section 12. These vest bracket means 16 and the support bracket means 23 are then tightened, resulting in the configuration of FIG. 1 for immobilizing the cervical spine. Thus a key advantage of the device and method is that standard vests can still be utilized in treatment of such injuries, since the continued use of a halo vest is usually required after complete confinement of the patient is no longer dictated, while the adaptations of the invention significantly improve patient recovery.

It is to be understood that the examples given above are for illustration purposes only, and that substitutions and equivalents may be obvious to those skilled in the art. The true scope and definition of the invention therefore is to be as set forth in the following claims.

I claim:

1. A device for cervical immobilization of an injured person, in combination with a bed frame having a horizontal rigid frame member positioned at one end of said bed frame, comprising:

an annular member adapted to be securely attached to a person's head;

vest means consisting of an anterior section having means to secure said vest to the person's torso;

anterior support rods attached to said vest;

posterior support rods attached to said horizontal rigid bed frame member by frame attachment means;

cross members attached to said annular member, each said cross member also being attached to one of said anterior support rods and one of s id posterior support rods.

2. The device of claim 1, further comprising a posterior section of said vest means attachable to said anterior section, wherein said frame attachment means are removable from said posterior support rods, and where said posterior support rods are attachable to said posterior section upon removal of said frame attachment means.

3. The device of claim 1, where said means for securing said anterior section to the person's torso comprise straps.

4. A method for cervical immobilization of an injured person in a bed having a rigid horizontal frame member, comprising the steps of:

providing a bed having a rigid horizontal frame member positioned at one end thereof, an annular member adapted for attachment to the head of a person, vest means consisting of an anterior section having means for securing said vest to the torso of the person, anterior support rods, posterior support rods, cross members, and attachment means;

attaching said annular member to the head of the person;

securing said vest means to the torso of the person;

attaching said cross members to said annular member;

attaching said anterior support rods to said anterior section of said vest means and to said cross members;

attaching said posterior support rods to said cross members and to said horizontal frame member;

such that all such attachments preclude movement of the various members relative to each other.

5. The method of claim 4, where said step of securing said vest means to the torso of said person is accomplished by encircling said torso with straps attached to said vest means.

6. The method of claim 4, where said step of securing said vest means to the torso of said person is accomplished by attaching said vest means to said bed by straps.

* * * * *